United States Patent [19]

Simpson et al.

[11] 4,220,621
[45] * Sep. 2, 1980

[54] BACKWASH SYSTEM FOR DILUTING APPARATUS

[75] Inventors: Ronald O. Simpson; Pedro P. Cabrera, both of Miami, Fla.

[73] Assignee: Coulter Electronics, Inc., Hialeah, Fla.

[*] Notice: The portion of the term of this patent subsequent to Apr. 10, 1996, has been disclaimed.

[21] Appl. No.: 14,306

[22] Filed: Feb. 23, 1979

Related U.S. Application Data

[63] Continuation-in-part of Ser. No. 906,235, May 15, 1978, Pat. No. 4,148,859.

[51] Int. Cl.² ............................................. G01N 1/14
[52] U.S. Cl. ................................. 422/103; 73/422 R; 422/100
[58] Field of Search .............. 422/103, 100; 73/422 R

[56] References Cited

U.S. PATENT DOCUMENTS

| | | | |
|---|---|---|---|
| 3,567,389 | 3/1971 | Coulter et al. | 422/103 |
| 3,567,390 | 3/1971 | Rothermel | 422/103 |
| 3,990,853 | 11/1976 | Godin | 422/103 |
| 3,991,055 | 11/1976 | Godin et al. | 422/103 |
| 4,148,859 | 4/1979 | Simpson | 422/103 |

*Primary Examiner*—R. E. Serwin
*Attorney, Agent, or Firm*—Silverman, Cass & Singer, Ltd.

[57] ABSTRACT

Improvements in a backwash system for diluting apparatus wherein a rinse solution is directed to and through a sample pick-up probe to a receptacle and therefrom to a waste depositary. Either the probe or the receptacle in turn is movable between a first uncoupled condition, along a predetermined or fixed path first to place the receptacle and the delivery end of the sample probe proximate, and second, to establish a fluid tight sealed coupling therebetween. The receptacle includes an entrance recess accommodating an apertured resilient insert which engages the delivery end of the probe to define the sealed coupling. A sensing switch is employed to assure that the rinse solution will not be dispensed as backwash unless the sealed coupling is known to have been established. The sensing switch can be presented in the path of the movable object, the switch being actuated when the movable object has completed its movement to establish the sealed coupling between the receptacle and the delivery end of the sample probe. The switch is scanned to ascertain its state and unless actuated, backwash is prevented.

Either both, one or the other of said receptacle and probe are mounted for singular or cooperative combined translatory movement, simultaneously or sequentially.

25 Claims, 8 Drawing Figures

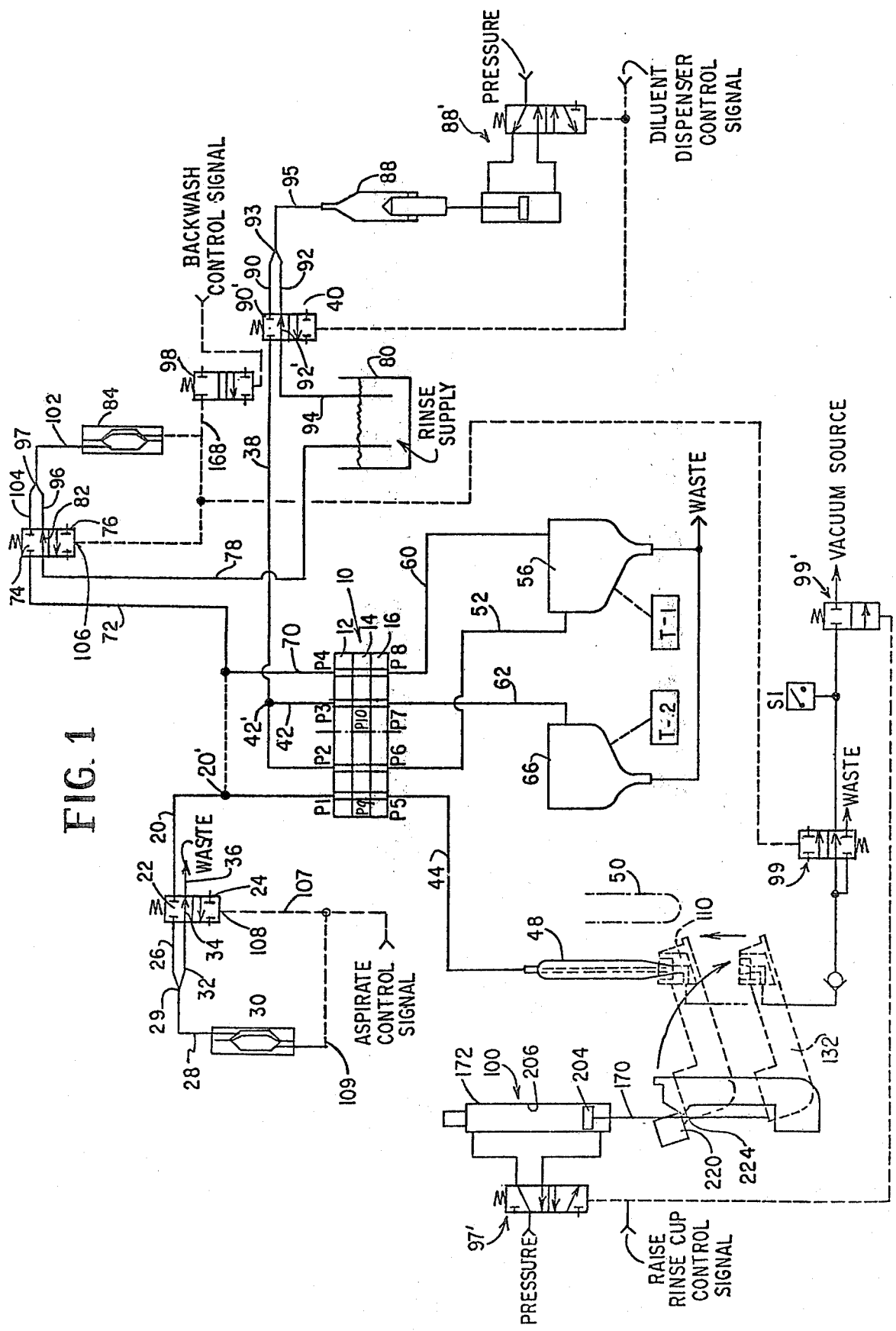

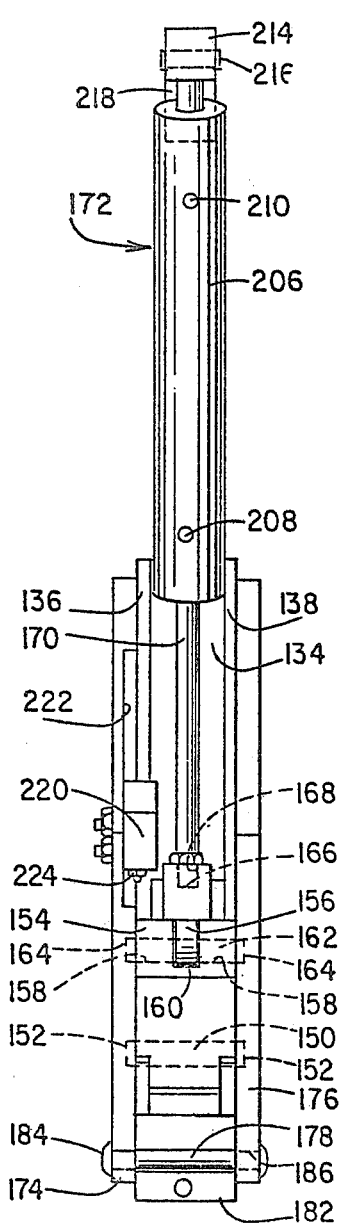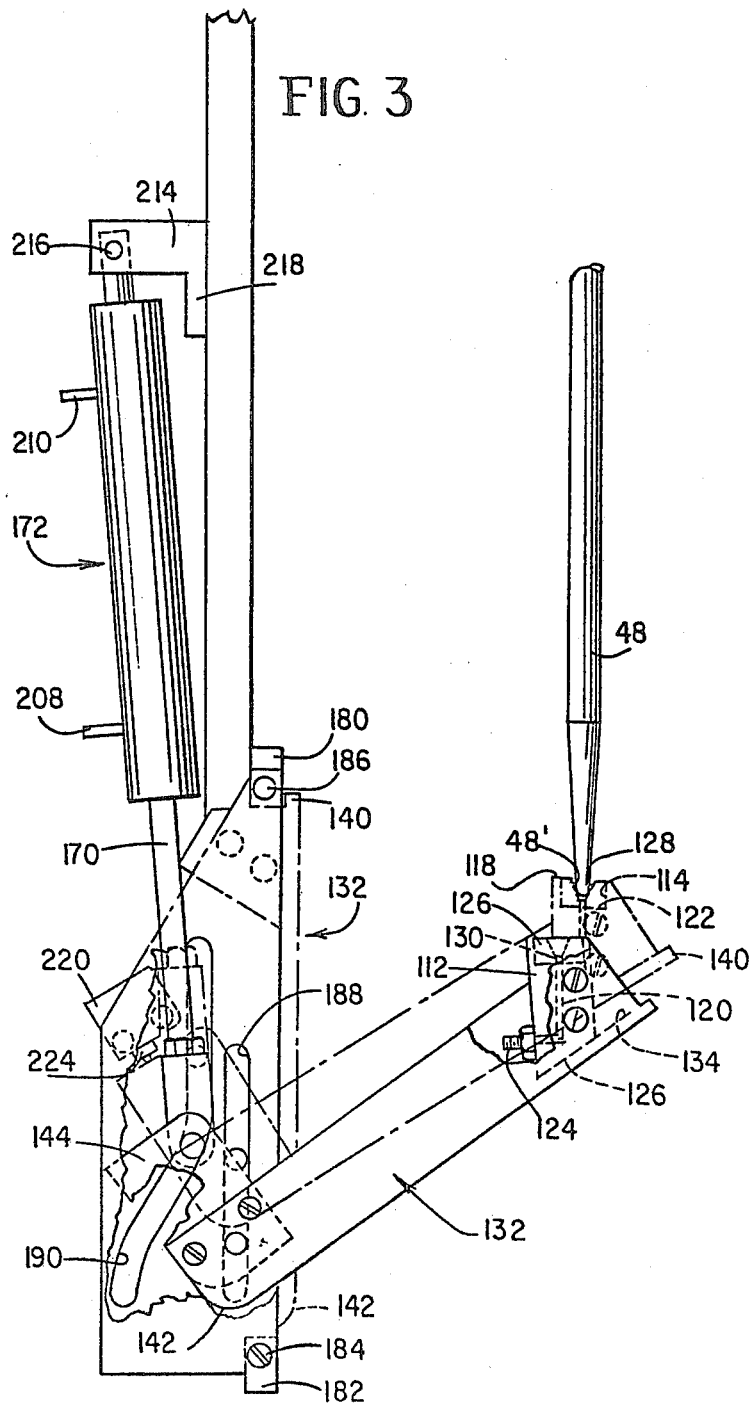

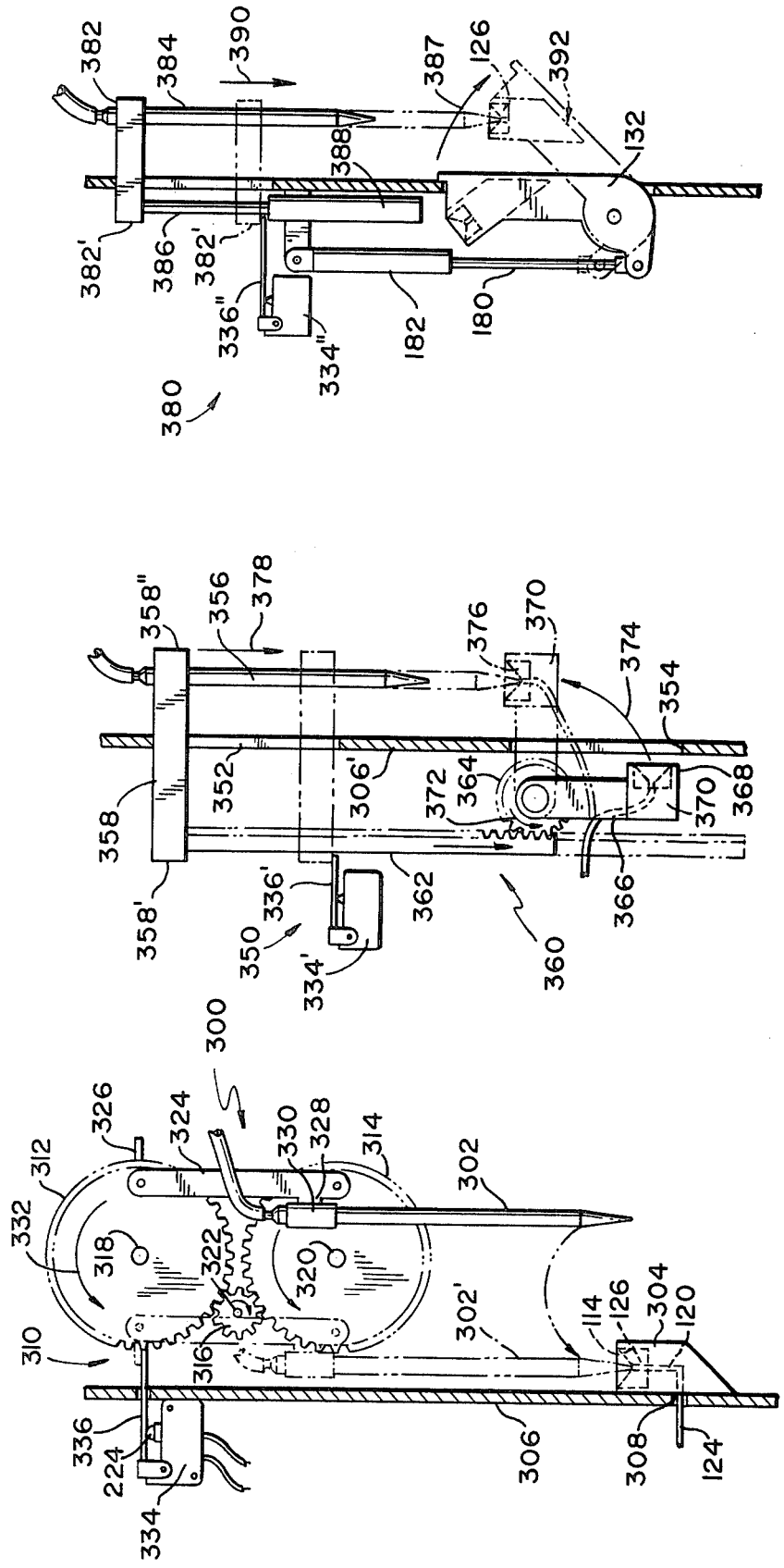

BACKWASH SYSTEM FOR DILUTING APPARATUS

CROSS-REFERENCE TO RELATED PATENTS

This patent application is a continuation-in-part of pending U.S. Patent Application Ser. No. 906,235 filed May 15, 1978, now U.S. Pat. No. 4,148,859 which application is incorporated by reference herein.

This patent application also presents improvements in a backwash system such as disclosed in U.S. Pat. No. 3,976,429 dated Aug. 24, 1976, said patent being hereby incorporated by reference in this application to supply additional background and explanation herein.

U.S. Pat. Nos. 3,549,994 and 3,567,390 dated respectively Dec. 22, 1970 and Mar. 2, 1971 likewise are incorporated by reference herein to serve as explanation of the types of apparatus in conjunction with which the improved backwash system can be employed.

BACKGROUND OF THE INVENTION

This invention relates generally to apparatus which utilizes vessels, valves and connecting conduits for the intermixing and/or diluting of fluids primarily for the purpose of making measurements and tests upon said fluid. More particularly, this invention is advantageously employed with the type of automatic analysis instrument such as disclosed in U.S. Pat. Nos. 3,549,994 and 3,567,390 which employs the Coulter particle analyzing principle disclosed in U.S. Pat. No. 2,656,508.

In U.S. Pat. No. 3,976,429, a backwash system was provided, including a dispensing cylinder and valve arrangement for directing diluent as a backwash from a source to a sampling valve utilized to make dilutions and then to a sampler in a form of an aspirator tube introduced into a fluid, and a vessel was provided for catching the backwash fluid. Means were provided for aspirating the backwash fluid to waste. The vessel and the aspirator tube were positioned one relative to the other to enable the backwash to be received in the vessel only when diluent was dispensed as backwash. One of the aspirator tube and collector vessel was returned to its so-called normal condition relative the other either by movement of the tube relative to the collector vessel, or by movement of the collector vessel relative to the tube. Suitable controls were provided to assure that the backwash occurs only when the tube and vessel were in a relative relationship to receive the backwash.

One structure described in the last-mentioned patent comprises a receptor vessel in the form of hollow, segmentally configured vessel having an inlet opening in one wall thereof. The vessel was mounted pivotally for selective limited rotation about an axis taken through a corner thereof. Gears were provided to effect pivotal movement of the vessel about the mounting axis to align the inlet opening with the aspirator tube so that backwashed diluent could be delivered from the aspirator tube to the inlet opening. The backwashed diluent received in the collector vessel was removed therefrom by drawing a vacuum upon the vessel, the line leading to a waste container distant from the apparatus.

Some problems have been encountered during use of said backwash system. One problem involves the manipulation of the receptacle from an inactive to a backwash receiving condition. The inlet opening of the receptacle had to be placed into a disposition proximate to the delivery end of the aspirator tube but was spaced therefrom. Thus in the course of delivery, some splashing would occur. Not only was there a chance that some delivered fluid would be lost but the problem of contamination of the environment is present. This is of particular disadvantage where the contents include contagions such as, for example, hepatitis causing organisms, possibly corrosive or chemically active fluids.

In the last mentioned patent, vacuum was only utilized to draw the backwash from the receptacle or collector vessel to a waste container. It also is important to provide means to establish a sealed coupling between the delivery end of the probe and the receptacle, and further, to provide means to assure that the backwash be effected only when a sealed connection has been effected between the delivery end of the aspirator tube and the means provided to receive the backwash fluid and the residual material driven out thereby.

The backwash system disclosed in pending patent application Ser. No. 906,235 employed a receptacle mounted on a carrier amd moved along a predetermined path first outward, then upward to engage the delivery end of the sample probe. The path of movement of the carrier properly to place the receptacle was defined by a guide track formed in a pair of guide plates. The receptacle included a resilient insert at its entrance or mouth capable of effecting a fluid tight sealed connection between the delivery end of the probe and the receptacle while reducing the mechanical shock of effecting such engagement. A switch was provided to guard against premature delivery of rinse fluid in the backwash cycle, that is, to permit delivery only if and when the receptacle is in proper position, sealingly coupled to the delivery end of the sample probe, the respective switch functioning in a fail safe sensing capacity.

SUMMARY OF THE INVENTION

In a backwash system of the general character described wherein a rinse fluid is driven back as backwash along the same path taken by sample from a sample probe, to be discharged to a receptacle sealingly coupled to said sample probe. One or both of the receptacle and the delivery end of the sample probe is movable along a predetermined path to a first condition proximate one another and a second condition sealingly engaged one with the other. Switch means are provided engageable by one of the movable members for sensing the establishment of the sealed condition and preventing premature feeding to discharge said rinse fluid from said delivery end. Movement to the first and second conditions can be in stages or continuous.

BRIEF DESCRIPTION OF THE DRAWINGS

FIG. 1 is a diagrammatic representation of one diluting system having the improved backwash system of the invention associated therewith;

FIG. 2 is an elevational view of the collecting apparatus employed in the backwash system according to the invention.

FIG. 3 is a side elevational view of the backwash collecting apparatus of FIG. 2 diagrammatically illustrating the operation thereof;

FIG. 6 is a diagrammatic representation of a further embodiment of the improved backwash system;

FIG. 7 is a diagrammatic representation of another embodiment of the improved backwash system; and FIG. 8 is a diagrammatic representation of a further modified embodiment of the invention.

DESCRIPTION OF PREFERRED EMBODIMENTS

Figure 4:
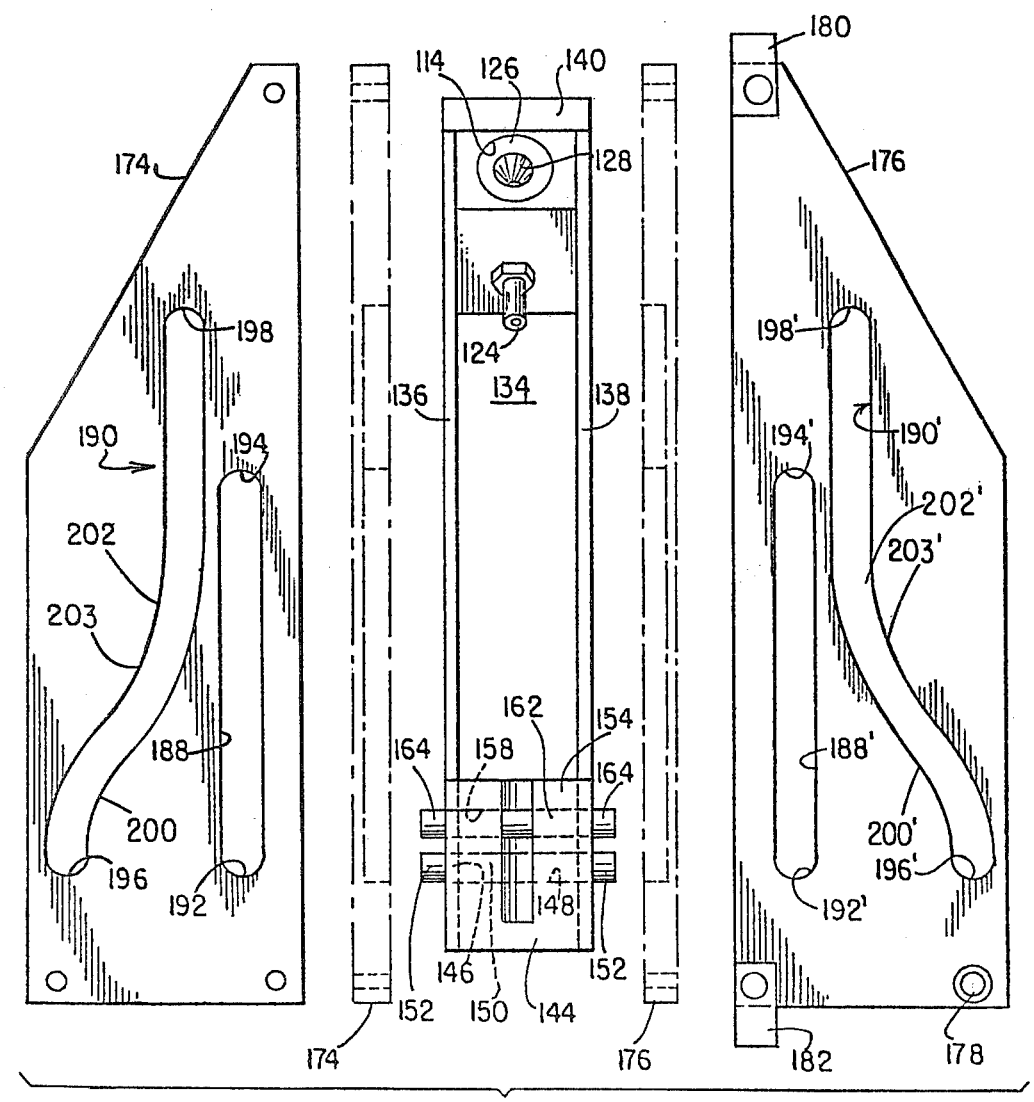
FIG. 4 is a diagrammatic partially exploded representation of the carrier, collector vessel and guide means used in the apparatus of FIGS. 2 and 3.

At the outset it would be convenient to outline the general scheme of the system of the invention by explaining the functions which are performed.

A fluid sample is obtained in any convenient manner.

An aspirator tube, referred to hereinafter as a semple probe, is introduced into the sample and a quantity of the sample is drawn into a first portion of the fluid transfer valve of the system. The valve operates to segment a minute measured part of the sample therein and such part is diluted with a predetermined quantity of diluent. The resulting suspension is transferred with the added diluent then to a testing apparatus wherein one or more tests or operations can be performed thereon. In the system of U.S. Pat. Nos. 3,549,994 and 3,567,390 a portion of a first diluted solution is taken from the first testing apparatus to the valve and directed, with a precise volume of diluent, into a second testing apparatus. Subsequent to segmentation and transfer, the valve is returned to its initiate or "sampling" position.

The backwash system according to the invention can be employed in another diluting system wherein a pair of different dilutions can be formed from the sample of whole blood by measuring and combining with diluent different volumes of said sample. These dilutions can be effected at the same time, with the sample and diluent units being directed simultaneously respectively to the pair of testing locations. The transfer valve rerturns to its initiate position and backwash therethrough can be effected.

With the last mentioned diluting system, only one backwash pump need be used for delivering rinse liquid to the two measuring portions of the valve simultaneously.

A detailed description and explanation of the structure and operation of diluting systems of the type described as well as the combination therewith, of testing apparatus operating on the Coulter principle is set forth in said U.S. Pat. Nos. 3,549,994; 3,567,390 and others. Principally, reference is made to U.S. Pat. Nos. 3,549,994 and 3,567,390 and each is hereby incorporated by reference herein as a part hereof.

In the system described in these patents, the sample consisted of whole blood. The blood sample tended to remain in the aspirator tube, and in the sample receiving portion of the transfer valve. Removal thereof from the aspirator tube was dependent upon the great volume of the next sample acting as a flushing agent. Additionally, the fluid transfer valve also required flushing to free same from the residual portions of the older sample whereby to prevent partial mixing or carry-over of successive samples. Obviously, carry-over of a part of a preceding sample will result in chance of error, particularly if there is much difference in characteristics between samples.

In U.S. Pat. No. 3,976,429 there was provided means for backwashing diluent in premeasured quantities through the fluid transfer valve and the aspirator tube in a predetermined time relationship relative to the programmed operaions, and, likewise, means were provided to coordinate the collection of the backwash and disposition of same, with the backwashing operation.

In the system provided in referenced U.S. Pat. No. 3,976,429, diluent was backflowed through the sample receiving passage of the fluid transfer valve to the sample probe which was utilized for sample intake. Coordinated with such operation, a waste collector vessel was arranged for disposition for receiving the backwash from the delivery end of the sample probe. The pivotally mounted collector vessel was mounted on a spring biased shaft, and caused to pivot at the time when the backwash is effected.

The collector vessel is coupled to a source of vacuum for directing the collected fluid to waste and a pump was used to drive the diluent to the receptacle.

Referring to FIG. 1, there is illustrated diagrammatically a diluting system similar to the system illustrated and described in U.S. Pat. Nos. 3,567,390 and 3,976,429. The control or fluid transfer valve provided for the careful measurement of the sample is designated generally by the reference character 10. Valve 10 is formed of three elements, an intermediate or center element 14 movable with respect to stationary outer elements 12 and 16. The elememts 12, 14 and 16 are arranged coaxially. The sandwiched or central element 14 is a carefully made and highly accurate structure having conduits P-9 and P-10, each on opposite sides of a central axis about which it is adapted to rotate. Each of these conduits is designed to carry a precise quantity or volume of some fluid, and upon movement between positions, there being two such positions, will slice off or subtend within itself the said volume of fluid and pass it or transfer it. This function is represented by the dashed lines showing the alignment of the conduits P9 and P10 with others carried by the stationary sandwiching members 12 and 16 of the valve 10. Although represented in the figure as a block or rectangular configuration, the valve 10 consisting of the elements 12, 14 and 16 preferably is cylindrical in configuration in accordance with and embodying the features of the valve illustrated specifically in FIGS. 6-10 of U.S. Pat. No. 3,567,390. The fluid transfer operation of valve 10 herein shall be described by reference only to the fluid passage means defined in the valve by which the transfer is effected and the respective dilutions made, schematically shown in rectangular configuration.

The outer members 12 and 16 are fixed relative to one another and each is provided with two pairs of ports or passageways. These are designated P1, P2, P3 and P4 in element 12 and P5, P6, P7, and P8 in element 16. When the center element 14 is in one position, say the first position, the left-hand conduit or passageway P9 is aligned with the passageways P1 and P5 at the same time that the right-hand conduit or passageway P10 is aligned with the passageways P3 and P7. Rotation of the center element 14 brings the passageways P9 and P10 to the positions represented by the dashed lines. Further flow between the passageways P1 and P5 is blocked as is further flow between the passageways P3 and P7. The passageway P9 is aligned with passageways P2 and P6 and the passageway P10 is aligned with passageways P4 and P8.

Rotation of the center element 14 is effective to slice or subtend a precise volume of fluid out of one path and enable it to be inserted into the other path while blocking off the first path. This is done in both positions of the transfer valve 10.

In one system illustrated herein as an example of a diluting system in which the backwash system of the invention can be usefully employed, the various fluid lines are described hereinafter for convenience, since the described system is only an example of the environment and does not form a part of the invention herein.

Fluid line 20 connects from the passageway P1 to the normally closed conduit 22 of pneumatically operated pinch valve 24, functionally equivalent in the illustrated system to the sample control valve to which reference is made in U.S. Pat. No. 3,567,390. Conduit 26 leads by way of line 28 of Y 29 to the sample pump which is shown in the form of a diaphragm type pump 30 or which can be an aspirator cylinder. Where a diaphragm type or other positive displacement pump is used, there is a lead to a source of alternating vacuum and pressure for operating the pump. Line 32 of Y connection 29 leads to normally open conduit 34 of pinch valve 24. Conduit 34 is coupled to waste W by line 36.

The diaphragm pump 30 and actuator 108 of valve 24 are coupled by lines 109 and 107 to the aspirator logic part of the overall program of the system.

Fluid line 38 connects from the passageway P2 to the line 90' of the diluent pinch valve 40.

Fluid line 42 connects from the passageway P3 to the fluid line 38 at point 42'.

Fluid line 44 connects from the passageway P5 to the sample probe or aspirator tube 48. Note that the delivery end 48' of probe 48 is adapted to dip into a sample source vessel 50 (broken outline). The vessel 50 is of any suitable construction and is withdrawn or otherwise removed when the requisite quantity of the sample has been aspirated therefrom.

Fluid line 52 connects from the passageway P6 to mixing vessel 56 for the testing apparatus T-1.

Fluid line 60 connects from mixing vessel 56 to the passageway P8 and is sometimes called a thief.

Fluid line 62 connects from the passageway P7 to mixing vessel 66 for the testing apparatus T-2.

Fluid line 70 connects from the passageway P4 also to line 20 and to the normally closed conduit 22 of sample control pinch valve 24.

Fluid line 72 leads from the normally closed conduit line 74 of control valve 76 to connect with line 20 at point 20' for diluent delivery.

Fluid line 78 leads from the diluent supply 80 to the normally open conduit 82 of the pneumatically operated pinch valve 76 functionally equivalent in the illustrated system to the sample control valve to which reference is made in U.S. Pat. No. 3,567,390. Conduit 96 leads by way of line 102 of Y 97 to the backwash dispenser which is shown in the form of a diaphragm type pump 84 or, which may be a dispensing cylinder. If a diaphragm pump or other positive displacement pump is used, there is a lead to a source or alternating vacuum and pressure for operating the pump. Line 104 of Y connection 97 leads to a normally closed conduit 74 of control valve 76.

The valve 24 has an intermediate condition where both conduits 22 and 34 are closed before the normally closed conduit 22 is opened. This operational characteristic assures clean separation during the operation of the valve 24.

Diluent pump 88 is connected by the lines 90 and 92 to the pinch valve 40. Pinch valve 40 may be identical in construction to pinch valves 24 and control valve 76. As mentioned, fluid line 38 is coupled to the normally closed conduit 90' of pinch valve 40. A fluid line 94 is coupled to the normally open conduit 92' from diluent supply 80. Fluid lines 90 and 92 of Y connection 93 couple valve 40 to diluent pump 88 by way of line 95. Pump 88 is operated by pressure arrangement 88'.

The sample and diluent pumps may be of any construction, but preferably are chambers having positive displacement means therein moving from end to end to displace a volume of fluid. Each pump draws into itself the same volume of fluid it is capable of pushing out.

Pump 88 may comprise a flexible diaphragm pump pneumatically operated by a source (of alternating vacuum and pressure). It has been found that a displacement pump comprising a chamber having a solid rod reciprocably driven through a seal with said chamber by an air cylinder, said cylinder being driven by introduction of pressurized air alternatively directed to either end of the cylinder is satisfactory.

The pump can include a spring to effect the return stroke which results in introduction of fluid into the last vacated chamber.

The improved backwash system of the invention is designated generally by reference character 100. The system 100 is capable of use with all the diluting systems referred to above and to other fluid moving systems as well and is coupled operationally to the diluent supply 80. Line 78 leads from the diluent supply 80 to normally open conduit 82 of backwash fluid control valve 76. Conduit 82 is coupled to one arm 96 of Y 97, with the leg 102 connected to dispenser 84. The other arm 104 of Y 97 is coupled to normally closed conduit 74 of control valve 76 and connects by line 72 to passageway P-1 of transfer valve 10.

The cylinder 172 is controlled by the operation of a solenoid operated valve 97' to effect raising of the piston 204 and plunger 170. The carrier 132 is pivoted to cause the receptacle 110 to be moved first outward. The carrier then is raised to cause the receptacle to be brought to a sealing coupling with the delivery end of the aspirator tube 48.

At the same time, valve 99' enables a vacuum to be drawn on the passage 120 of receptacle 110. Check switch $S_1$ controls a solenoid valve 98 which controls the operation of pump 84 and, as well, operates to control operation of valve 99 to enable flow to waste. After a suitable elapse of time, the switch $S_1$ is scanned electronically, to sense if it is open or closed. If open, it indicates failure of the sealed connection between tube 48 and cup 110 to be established as a high vacuum is drawn to operate and close switch $S_1$ when a sealed engagement of receptacle and probe (tube) is established.

When proper seating is established, solenoid operated valve 98 is energized, causing the pump 84 to operate to cause rinse liquid to be dispensed; also, valve 99 is opened to enable flow to waste. Deenergizing solenoid operated valve 97' causes the receptacle to be retracted by reverse operation of piston 204.

It should be understood, that where microswitch 220 is utilized, the effect of operation of switch $S_1$ is met by the operation of switch 220, switch $S_1$ not being used though it may be present in the system. Both switches 220 and $S_1$ can be operative as a fail safe device so that both have to operate to effect backwash.

At this time attention is directed to the collector vessel 110 and its mounting as illustrated in FIGS. 2 and 3. The collector vessel 110 has a body 112 of generally rectangular configuration. A recess 114 of generally right-cylindrical configuration is formed in body 112 opening to the top wall 118 thereof. A bore 120 is formed through the body 112 communicating between the floor 122 of recess 114 and a fitting 124.

A generally cylindrical insert 126 of size and conforming configuration to recess 114 is tightly engaged within the recess 114. The insert 126 preferably is formed of a chemically resistant material such as one of the silicone rubbers. Insert 126 has a conical recess 128 and a through passage 130 at the bottom of recess 128. When the insert 126 is seated within recess 114, the passage 130 is coaxial with and sealingly communicates with the entry to bore 120 of vessel 110, and the recess 128 opens to the top wall of vessel 110 with the insert flush with said top wall. The base 126 of vessel 110 is angular to facilitate seating of the vessel in carrier trough 132.

The carrier trough 132 is defined by planar floor 134 and a pair of upright parallel side walls 136 and 138. The floor 134 extends outward of the walls 136 and 138 to define ledge 140. The opposite end of trough 132 is rounded, as shown at 142, with the floor 134 spaced inward of the near ends of side walls 136 and 138.

Clevis block 144 is fixedly secured to the trough 132 between walls 136 and 138 thereof adjacent rounded portion 142. Coaxial passages 146 are formed in walls 136 and 138, with bore 148 (FIG. 4) formed through clevis block 144. A pin 150 is tightly seated through the said coaxial passages and bore 148, opposite ends 152 of pin 150 extending outward from the walls 136,138 when the clevis block 144 is installed.

Clevis block 144 includes spaced wall portions 154 capable of accommodating clevis 156 therebetween. A pair of aligned passages 158 are formed through walls 154. Clevis 156 carries passage 160 which is aligned axially with passages 158. Pin 162 is seated through passages 158 and 160 to retain the clevis 156, opposite ends 164 of pin 162 extending outward on opposite sides of the clevis block. Portion 166 of clevis 156 carries a threaded socket 168 for receiving the threaded end of plunger 170 of air cylinder 172.

Referring to FIGS. 3 and 4, guide plates 174 and 176 are arranged upright and spaced apart by spacers 178, 180 and 182 and are secured fixed in such array by fastening means such as screws 184 seated in threaded passageways 186 formed in the spacers 178, 180 and 182 to define a frame. Each of the plates 174 and 176 carry a pair of grooves, 188 and 190 in plate 174, and 188' and 190' in plate 176. Grooves 188 and 188' are linear and have opposite ends 192, 194 and 192', 194' respectively. Grooves 190 and 190' are longer than grooves 188 and 188'. The grooves 190 and 190' have opposite ends 196, 198 and 196', 198' respectively. Ends 196 and 196' are aligned and are spaced by a distance equal to the axial distance between pins 150 and 162. The distances between ends 194 and 198 and between ends 194' and 198' likewise are equal to the axial distance between pins 150 and 162. Each of grooves 190, 190' have a curved portion 200 and 200' leading from ends 196, 196' to a location 202, 202' from whence the grooves 190, 190' proceed along a line parallel to the grooves 188 and 188' to ends 194, 194'.

When the plates 174 and 176 are assembled to define a frame, groove 188 and groove 190 run coextensive with groove 188' and groove 190', with the ends 152 (of pin 150) and 164 (of pin 162) seated therein, thereby defining a track along which the said pin ends can run. Ends 152 of pin 150 are seated in the grooves 188, 188' while the ends 164 of pin 162 are seated in grooves 190, 190'.

As illustrated in FIGS. 2 and 3, plunger 170 is secured to a position 204 ridable within cylinder 206 which carries inlet and outlet fittings 208, 210, coupled to a source of air pressure (not shown) through suitable valving and controls related to the operations of the diluent dispenser. The upper or free end is seated in clevis 214 by pin 216, clevis 214 formed on mounting member 218.

The collector vessel 110 is secured within the carrier trough 132 at the end thereof adjacent ledge 140 with the angular base 126 engaged on floor 134 so that the axis of the recess is angular relative to the walls 136 and 128 of the trough 132.

During the time of the program of the apparatus while the backwash cycle is inoperative, the trough 132 is recessed within the frame defined by the guide plates 174 and 176, the plunger 170 of air cylinder 172 being extended and the pin ends 152 seated at ends 192, 192' of grooves 188, 188' and pin ends 164 seated near ends 196, 196' of grooves 190, 190'. Grooves 190, 190' may be slightly longer than necessary to provide some over travel capability for tolerance reasons. The inward travel of trough 132 is halted when the ledge 140 strikes the surface to which spacers 180, 182 are mounted. When the backwash cycle is reached, air pressure is introduced to the cylinder 206 of air cylinder 172 through inlet 208 forcing the piston 204 upward and carrying the plunger 170 into the cylinder 206. Since the clevis 156 is secured to the clevis block 144 by pin 162, withdrawal of the plunger 170 pulls the pin ends 164 along the curved portions 200, 200' of grooves 190, 190', with pin ends 152 remaining at ends 192, 192' of grooves 188, 188' and the trough 132 pivoting about said pin 150 at said groove ends 192, 192'. The pin ends 164 will ride in curved portions 200, 200' until a location 203, 203' (near location 202, 202') is reached. Continued withdrawal of the plunger 170 into cylinder 206 pulls pin ends 164 along the remaining portions of grooves 190, 190'. At location 202, 202', the pivotal movement of the trough 132 slows. As the ends 164 travel up the remaining portion of the curves, pivotal motion gradually decreases as pin ends 152 gradually accelerate along grooves 188, 188'. The trough 132 is fully, outwardly, angularly extended relative to the guide plates 174, 176. The vessel 110 is arranged below the delivery end of the sample probe 48 with the passage 130 coaxial with the delivery end 48' of said sample probe 48.

Further continued withdrawal of the plunger 70 causes both pin ends 152 and 164 to move in unison until they approach ends 194, 198 and 194', 198' of grooves 188, 188' and 190, 190'. Travel is halted by the action of the probe in the rinse cup and/or the engagement of clevis 144 with the microswitch 220. Thus the delivery end of sample probe 48 engages sealingly within the conical recess 128 of insert 126 and a sealed connection is established to the bore 120 of said vessel. The continuing push of the piston 204 upwards continues the firm seating of the delivery end 48' against insert 126.

The diluent is discharged to the transfer valve 10 and backwashed through line 44 to sample probe 48 and its delivery end 48' to the bore 120 and thence to a waste depositary W. No splash occurs, of course, between the delivery end of probe 48 and the collector vessel 110. Only when backwashing is completed is air introduced into cylinder 206 by way of outlet 210 forcing the piston 204 to move in an opposite direction and causing the plunger 170 to be forced outward of cylinder 206. The pin ends are directed along the respective grooves retracing the same path in return so that the collector vessel 110 is lowered first and then the trough 132 is pivoted toward the guide plates 174, 176 to a retracted condition within the frame defined thereby.

The spacers 180 and 182 serve as mounting block means for the assembly of plates 176, 176 so that the guide plate assembly is installed upon the diluting apparatus at a location whereat the fully completed path of the carrier 132 places the collector vessel 110 in correct position to establish the sealed coupling with the delivery end of the aspirator tube 48 for the backwash cycle to be implemented.

As mentioned earlier, the microswitch 220 may be installed instead of vacuum switch $S_1$.

The microswitch 220 can be seated within a suitable recess 222 in the plate 174 with its actuator 224 seated in the path taken by clevis block 144. The actuator 224 is intercepted by block 144 when the carrier 132 of collector vessel 110 has reached its position of extension and has moved to place the pin ends 152 and 164 near the uppermost ends of their respective tracks. At this time the collector vessel 110 is capable of receiving the delivery end 48' of the aspirator tube in a sealed engagement in the conical recess 128 of insert 126.

Figure 5:
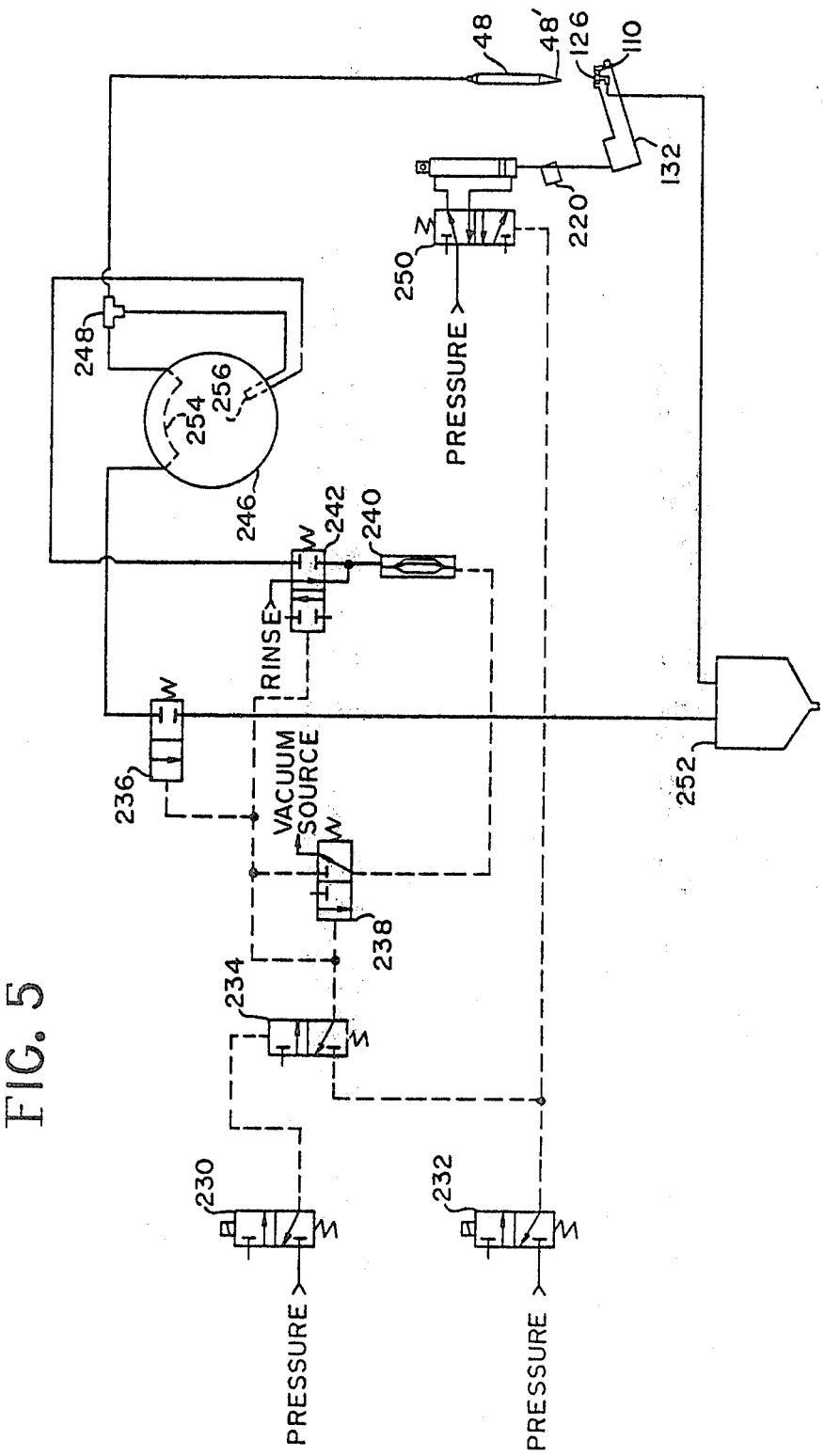
FIG. 5 is a diagrammatic representation of a modified diluting system having the improved backwash system of the invention associated therewith.

The modified diluting system with which the improved backwash system of this invention can be employed has been diagrammatically illustrated in FIG. 5 and does not employ a thief for directing a portion of the first dilution to a segmenting portion of the transfer valve for making a second dilution thereof. The required pair of different dilutions are effected simultaneously by utilizing a transfer valve 246 having passage means therein for isolating two different volumes of sample at the same time. Thus only a single pump is required to introduce rinse liquid as backwash to one portion 256 of said passage means and from there, the rinse liquid is directed through the other portion 254 of the valve 246 and thence, to the aspirator tube.

In order to avoid harmful effects possible due to surges of liquid, say due to temporary blockage in the conduit means, for example, diverter means 248 are inserted in the outlet path of the rinse liquid from valve portion 256. The flow of rinse liquid is split into two flows, one being led directly to the other measuring portion 254 of the valve while the other is directed to the backwash receptacle 110 via the aspirator tube 48. The rinse liquid outlet of said one portion 254 leads to valve 236 and thence to a waste collector 252.

In the system of FIG. 5, the solenoid 232 is operated to switch valve 250 and effectively cause the carrier 132 first to be raised placing receptacle 110 outward, and then the carrier further is moved upward to seat insert 126 against end 48' of tube 48. When the sealed connection between insert 126 and end 48' is made, switch 222 is closed. Closure of switch 222 operates solenoid 230 to open normally closed valve 234. Valve 234 is coupled to the output of valve 232. Valve 234 also operates to open both valves 236 and 242 simultaneously. These valves 236 and 242 must be open so that when the pump 240 is operated by operation of valve 238, the rinse liquid can pass to the transfer valve 246.

Actuation of valve 234 causes valve 238 to operate to dispense rinse liquid by actuating pump 240. The flow emerges from one portion of the valve 246 and is split by valve 248, one portion being directed to tube 48 and the other being directed to the other measuring portion of the valve 246 and thence back to valve 236 and waste 252. The solenoid control valve 232 then operates to lower the receptacle 110 and loads the pump 240 with a volume of rinse fluid. The system then is ready for the next test.

Referring now to FIG. 6, there is illustrated a backwash system generally designated by reference character 300 which differs from system 100 in the fact that the probe 302 is movable while the receptacle 304 is secured to upright wall 306. The vessel 304 is constructed substantially the same as that of vessel 110 having insert 126 seated in the recess 114 and passage 120 leading to fitting 124 passing through aperture 308 formed in wall 306.

There is provided a driven gear system 310 including gears 312 and 314 arranged one above the other and coupled by transfer gear 316. The axes 318 and 320 of said gears 312 and 314 are parallel and superposed with the axis 322 of transfer gear 316 between and offset from axes 318 and 320. Both gears 312 and 314 are mounted for counter clockwise rotation. Connecting rod 324 couples the pair of gears 312 and 314. Gear 312 carries a trip lever 326 extending outward circumferentially therefrom. Connecting rod 324 includes an extension 328 on which is mounted support 330 capable of accommodating probe 302.

When gear 312 is rotated counter-clockwise (see arrow 332), gear 314 likewise is rotated in the same direction through gear 316. The microswitch 334 which includes actuating lever 336 is identical to switch 220 in function.

Upon the occurrence of the suitable signal desiring backwash, the gear 312 is rotated 180° carrying the probe 302 to the condition represented by the broken outline, designated 302'. The trip lever 326 engages the actuating lever 336 of switch 334 which causes pin 224 to close switch 334. The fact of closure of switch 334 is monitored and when confirmed, backwash is effected by enabling the operation of the pump 80 to drive rinse liquid through the delivery end of probe 302 into receptacle 304.

FIG. 7 illustrates, diagrammatically, a further modification of the backwash system according to the invention. System 350 differs from system 100 and 300 in that both the sample probe and the receptacle are mobile simultaneously to effect sealed engagement of the probe and receptacle.

Wall 306' is provided with openings 352 and 354. A rack and pinion translation mechanism 360 is provided to effect said simultaneous movement and consists of a downwardly depending toothed rack 362 secured to the probe support 358. The rack 362 is spaced inwardly from one end 358' of the support 358 while the probe 356 is located adjacent end 358" of said support 358. The rack 362 is oriented parallel to the probe 356.

Pinion gear 364 is arranged to mesh with rack 362 in a first condition at its lowermost end of said rack. Carriage 366 is secured rigidly to pinion gear 364 and has a free end 368 whereat receptacle 370 is secured. At the first condition of the rack and pinion mechanism 360, the support member 358 is located adjacent the upper end of wall opening 352 and the carriage 366 is oriented downward with the free end thereof at the level of the lower end of opening 354 and adjacent thereto.

Rotation of the pinion gear 364 in a counterclockwise direction (see arrow 372) causes the carriage 366 to swing in an angular direction indicated by arrow 374, placing the receptacle 370 in a second condition where the entrance 376 thereof is located below the delivery end of probe 356 as shown in broken line representation. Simultaneously with the angular motion of the carriage 366 and receptacle 370, the support member 358 is caused to be translated in the direction of 378.

Linear movement of the rack 362 causes the support member 358 to be translated downward, that is, lowered to meet the receptacle, that is, to engage the delivery end of probe 356 within the recess 376 of receptacle vessel 370 in the sealed coupling desired.

Microswitch 334' is located with its actuating lever 336' in the path of end 358' of support member 358 so that the switch is triggered closed when a predetermined distance of travel of said support member 358 has been reached to confirm the establishment of the sealed coupling of probe and receptacle vessel.

Referring to FIG. 8, there is illustrated a further embodiment 380 of the invention wherein the receptacle is swung outwardly, as described in respect of system 100 and a second cylinder and plunger arrangement is provided to move the probe toward the receptacle, instead of continuing the movement of the receptacle to establish the sealed engagement as described in respect of the structure illustrated in FIGS. 1 to 4.

A horizontally oriented support has sample probe 384 seated at one end thereof oriented in a downwardly direction. The plunger 386 of cylinder 388 is in extended condition with the support 382 located in its raised condition, shown in full line representation. The cylinder, carriage and receptacle are substantially identical with the arrangement illustrated in FIGS. 2 to 4 except the portion 190' of the track 190 is required to be present. Only portions 200, 203 and 202 are required.

When the cylinder 182 is operated to withdraw plunger 180, the carriage 132 is moved swingably (arrow 387) to the condition illustrated in FIG. 1. The plunger 386 is withdrawn, causing the support 382 to be translated in the direction of the arrow 390, toward and then into sealed engagement within the insert 126 at the entrance to said receptacle vessel 392. The support end 382' engages actuating lever 336" of switch 334" when the full extent of the path of said support 382 has been reached. At that position, the delivery end of the probe and the receptacle are sealingly engaged to permit actual backwash to be effected, as confirmed by the actuation of switch 334".

It will be noted that the translation of the movable one of said probe and receptacle or both, as illustrated in FIGS. 6 to 8 can be a continuous movement rather than one where there are stages, that is, one condition proximate, and then further movement to the sealed engaged condition. This is particularly the case in respect of FIGS. 6 and 7.

It also should be understood that the resilient member described herein as an insert received with the entrance to the receptacle, such resilient member could be a ring or the like carried by the probe and adapted to be received within the entrance to the receptacle to effect the described sealed coupling therebetween.

Minor variations may be effected in the illustrated and described structures without departing from the spirit and scope of the invention as set forth in the appended claims.

What we claim is:

1. A backwash system capable of being operationally coupled for use with a diluting system of the type including probe means which include a probe having a combined intake and delivery end, a source of diluent and conduit means linking said diluent source to said probe means, and said backwash system arranged to pass diluent as rinse fluid from the source thereof to and through the delivery end of the probe along the path taken during intake but in a direction opposite thereto at a predetermined stage in the operation of the diluting system, and a receptacle vessel for receiving the backwashed liquid from the probe means, means carried by one of said receptacle vessel and probe means to establish a sealed engagement therebetween, means mounting said probe means and said receptacle vessel for relative movement along a predetermined path between a location displaced from the delivery end of said probe means and a location engaging the delivery end of said probe means in a sealed coupling therewith, means defining said path of movement, drive means moving at least one of said receptacle vessel and probe means along said path of movement.

2. The combination as claimed in claim 1 and fail-safe switch means operable only upon establishment of said sealed coupling to permit delivery of diluent to said probe means as backwash.

3. The combination as claimed in claim 2 having a source of pressure and vacuum, control means operating to permit passage of diluent to said probe means, and said fail-safe switch means includes a check switch coupled to said control means for enabling of same between first and second conditions, and means coupling said vessel to said vacuum source, said means also coupled to said check switch.

4. The combination as claimed in claim 2 and means coupling said vessel to said vacuum source.

5. The combination as claimed in claim 2 in which said switch means includes actuator means disposed in the path of movement and adapted to be engaged only when said moved one has reached a position establishing the sealed connection between the receptacle vessel and the delivery end of the probe means.

6. The combination as claimed in claim 1 and means for storing and delivering a known volume of diluent from said source and including a pneumatically controlled pump, and switch means arranged to permit said pump to be energized only when the sealed coupling has been effected between the delivery end of the probe means and the receptacle vessel.

7. The combination as claimed in claim 2 and means for storing and delivering diluent from said source and including a pneumatically controlled pump, a solenoid valve to control said pump and said switch means is arranged to permit said pump to be energized only when the sealed coupling has been established and confirmed by operation of said switch means.

8. The combination as claimed in claim 1 in which said receptacle vessel comprises a body having a top opening recess, an internal bore leading from said recess through said body to the exterior thereof and said means to establish a sealed engagement comprise a resilient insert tightly seated within said recess, said insert having a top opening cavity and passage means communicating to said bore, said cavity capable of being engaged by the delivery end of the probe means whereby to establish said sealed coupling, and means for coupling said source of vacuum to the other end of said internal bore.

9. The combination as claimed in claim 1 and pump means for storing and delivering diluent to said probe means, a valve means for operating said pump and switch means comprising a microswitch arranged to energize said valve means for operating said pump only when the relationship of position of said carriage reaches a position effecting the sealed connection between the delivery end of the probe means and the receptacle.

10. The combination as claimed in claim 2 in which said switch means includes a microswitch disposed in the path of movement and engageable only when the movable one of said receptacle vessel and probe means has been moved sufficiently so that the receptacle vessel is in condition sealingly to be coupled to the delivery end of the probe means.

11. The combination as claimed in claim 1 in which said probe means and said receptacle vessel are movable to establish said sealed coupling therebetween.

12. The combination as claimed in claim 1 wherein said receptacle vessel and probe means are movable simultaneously.

13. The combination as claimed in claim 1 wherein said receptacle vessel and probe means are movable sequentially.

14. The combination as claimed in claim 1 in which the receptacle vessel is translated to a position below the delivery end of said probe means proximate same and said probe means then is translated toward said receptacle vessel to establish said sealed coupling.

15. The combination as claimed in claim 1 in which the probe means are translated and the receptacle vessel is stationary.

16. The combination as claimed in claim 1 in which said mounting means for said probe means comprise a support member carrying same and gear means coupled to said support member for moving said probe means between said locations.

17. The combination as claimed in claim 16 in which said gear means include a gear train and said support member comprises a connecting link coupled to said gear train and carrying said probe means depending therefrom, said probe means occupying parallel planes at both locations, rotation of said gear means effecting movement of said probe means between said locations.

18. The combination as claimed in claim 1 in which the mounting means for said probe means comprise a support member carrying same, said means for effecting movement of said probe means and receptacle vessel comprise a rack and pinion arrangement, the rack being coupled to said support member and the pinion being coupled to said mounting for said receptacle vessel for pivoting same to place said receptacle vessel in said sealed engagement.

19. The combination as claimed in claim 17 in which the path of movement of said probe means defines a parallelogram.

20. The combination as claimed in claim 19 and a trip lever carried by one of said gear train, the switch means disposed in intercepting relationship relative the path taken by said trip lever.

21. The combination as claimed in claim 16 wherein said gear means includes rack and pinion means, said rack secured on said support and coupled operatively to said pinion gear means, said pinion gear means coupled operationally to the means mounting said receptacle vessel.

22. The combination as claimed in claim 16 and sensing means arranged in intercepting relation to the path of movement for engagement when said sealed coupling is effected and means coupled to said sensing means to cause delivery of rinse fluid only when said sensing means confirms said sealed engagement.

23. The combination as claimed in claim 15 and at least one fluid pressure operated cylinder and plunger operably coupled to said mounting for moving said receptacle vessel at least to said first location and means operable upon one of said receptacle vessel and support member to move same for effecting said sealed coupling.

24. The combination as claimed in claim 23 and a second fluid pressure operated cylinder and plunger operably coupled to said support member for moving said probe means towards said receptacle vessel to effect said sealed coupling therebetween at said second location.

25. The combination as claimed in claim 24 in which the movement of probe means and receptacle vessel are simultaneous.

* * * * *